US010859857B2

(12) United States Patent
Brennan et al.

(10) Patent No.: US 10,859,857 B2
(45) Date of Patent: Dec. 8, 2020

(54) PULSED PLUS LENS DESIGNS FOR MYOPIA CONTROL, ENHANCED DEPTH OF FOCUS AND PRESBYOPIA CORRECTION

(71) Applicant: Johnson & Johnson Vision Care, Inc., Jacksonville, FL (US)

(72) Inventors: Noel A. Brennan, Jacksonville, FL (US); Salvatore Caldarise, St. Johns, FL (US); Khaled Chehab, Jacksonville, FL (US); Xu Cheng, St. Johns, FL (US); Michael J. Collins, Jollys Lookout (AU); Brett A. Davis, Holland Park (AU); Jaclyn Hernandez, Jacksonville, FL (US); Adam Toner, Jacksonville, FL (US); Fan Yi, Stafford Heights (AU)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 94 days.

(21) Appl. No.: 15/459,308

(22) Filed: Mar. 15, 2017

(65) Prior Publication Data

US 2017/0276963 A1    Sep. 28, 2017

Related U.S. Application Data

(60) Provisional application No. 62/311,485, filed on Mar. 22, 2016.

(51) Int. Cl.
*G02C 7/00* (2006.01)
*G02C 7/02* (2006.01)
(Continued)

(52) U.S. Cl.
CPC ............... *G02C 7/081* (2013.01); *G02B 3/14* (2013.01); *G02B 27/0075* (2013.01); *G02C 7/04* (2013.01);
(Continued)

(58) Field of Classification Search
CPC .. A61F 2/16; A61F 2/145; A61F 2/164; A61F 2/1613; A61F 2/1616;
(Continued)

(56) References Cited

U.S. PATENT DOCUMENTS

| 4,279,474 A | 7/1981 | Belgorod |
| 5,712,721 A * | 1/1998 | Large ................... A61F 2/1613 351/158 |

(Continued)

FOREIGN PATENT DOCUMENTS

| RU | 2570287 C2 | 12/2015 |
| TW | 201502645 | 1/2015 |

(Continued)

OTHER PUBLICATIONS

Singapore Search Report for corresponding SG Appln. No. 10201702281T dated Jan. 2, 2018.
(Continued)

*Primary Examiner* — Mustak Choudhury

(57) ABSTRACT

Ophthalmic lenses incorporate multifocal properties for the purpose of slowing, retarding, controlling or preventing myopia development or progression, correcting presbyopic vision or allowing extended depth of focus. The lens has electronically controlled adjustable focus where the change in focus oscillates so rapidly that it is imperceptible to human vision.

21 Claims, 8 Drawing Sheets

(51) Int. Cl.
*G02C 7/04* (2006.01)
*G02C 7/08* (2006.01)
*G02B 3/14* (2006.01)
*G02C 7/06* (2006.01)
*G02B 27/00* (2006.01)
*A61F 2/16* (2006.01)

(52) U.S. Cl.
CPC ............... *G02C 7/041* (2013.01); *G02C 7/06* (2013.01); *G02C 7/083* (2013.01); *G02C 7/085* (2013.01); *A61F 2/1624* (2013.01); *G02C 2202/24* (2013.01)

(58) Field of Classification Search
CPC .... A61F 2/1624; A61F 2/1627; A61F 2/1654; G02C 7/04; G02C 7/022; G02C 7/049; G02C 7/048; G02C 7/081; G02C 7/041; G02C 7/042; G02C 7/043; G02C 7/06; G02C 7/083; G02C 7/085; G02C 7/12; G02C 7/101; G02B 1/043; G02B 3/14; G02B 26/004; G02B 27/0025; G02B 27/0075; H05K 1/0274; H05K 1/189; H05K 3/301
USPC .... 351/158, 159.03, 159.01, 159.02, 159.46, 351/159.39, 41, 44; 359/483.01, 245, 359/256, 558; 623/6.22, 6.23, 6.11; 349/13, 16
See application file for complete search history.

(56) References Cited

U.S. PATENT DOCUMENTS

| | | | |
|---|---|---|---|
| 5,838,419 A | 11/1998 | Holland | |
| 6,511,175 B2 | 1/2003 | Hay | |
| 7,423,801 B2 | 9/2008 | Kaufman et al. | |
| 8,542,325 B2 | 9/2013 | Burton | |
| 8,764,185 B1 | 7/2014 | Biederman et al. | |
| 8,906,088 B2 | 12/2014 | Pugh et al. | |
| 9,052,528 B2 | 6/2015 | Pugh | |
| 9,155,614 B2 | 10/2015 | Blum et al. | |
| 9,289,623 B2 | 3/2016 | Pugh et al. | |
| 9,351,827 B2 | 5/2016 | Toner et al. | |
| 2007/0052876 A1* | 3/2007 | Kaufman | G02B 3/14 349/13 |
| 2008/0024858 A1 | 1/2008 | Kaufman | |
| 2009/0135372 A1* | 5/2009 | Sarver | A61B 3/1015 351/212 |
| 2009/0192437 A1 | 7/2009 | Soltz et al. | |
| 2009/0268154 A1 | 10/2009 | Meyers et al. | |
| 2010/0149073 A1* | 6/2010 | Chaum | G02B 27/0093 345/8 |
| 2012/0062836 A1* | 3/2012 | Tse | G02C 7/042 351/159.41 |
| 2013/0258275 A1* | 10/2013 | Toner | G02C 7/04 351/159.03 |
| 2014/0240665 A1 | 8/2014 | Pugh | |
| 2015/0312560 A1* | 10/2015 | Deering | G02B 13/0085 345/1.3 |
| 2016/0054588 A1 | 2/2016 | Brennan et al. | |
| 2016/0128562 A1* | 5/2016 | Durr | A61B 5/7415 351/205 |
| 2016/0175181 A1 | 6/2016 | Du | |

FOREIGN PATENT DOCUMENTS

| | | |
|---|---|---|
| WO | WO2005/033782 A2 | 4/2005 |
| WO | WO2011/153112 A2 | 2/2011 |
| WO | WO2015024328 A1 | 2/2015 |

OTHER PUBLICATIONS

Search Report for corresponding Russian Appln. No. 2017109380/28 dated Apr. 27, 2018.

Papadatou et. al. "Temporal Multiplexing with Adaptive Optics for Simultaneous Vision" Biomedical Optics Express vol. 7, No. 10 (Oct. 2016).

* cited by examiner

FIG. 2
Condition 1
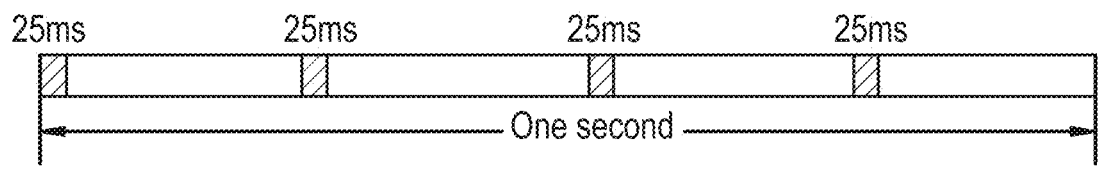
Condition 2
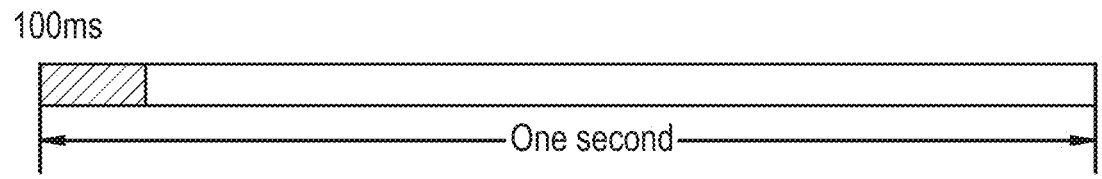
▨ +3D
☐ Plano

Visual Acuity (N=4)

Contrast sensitivity

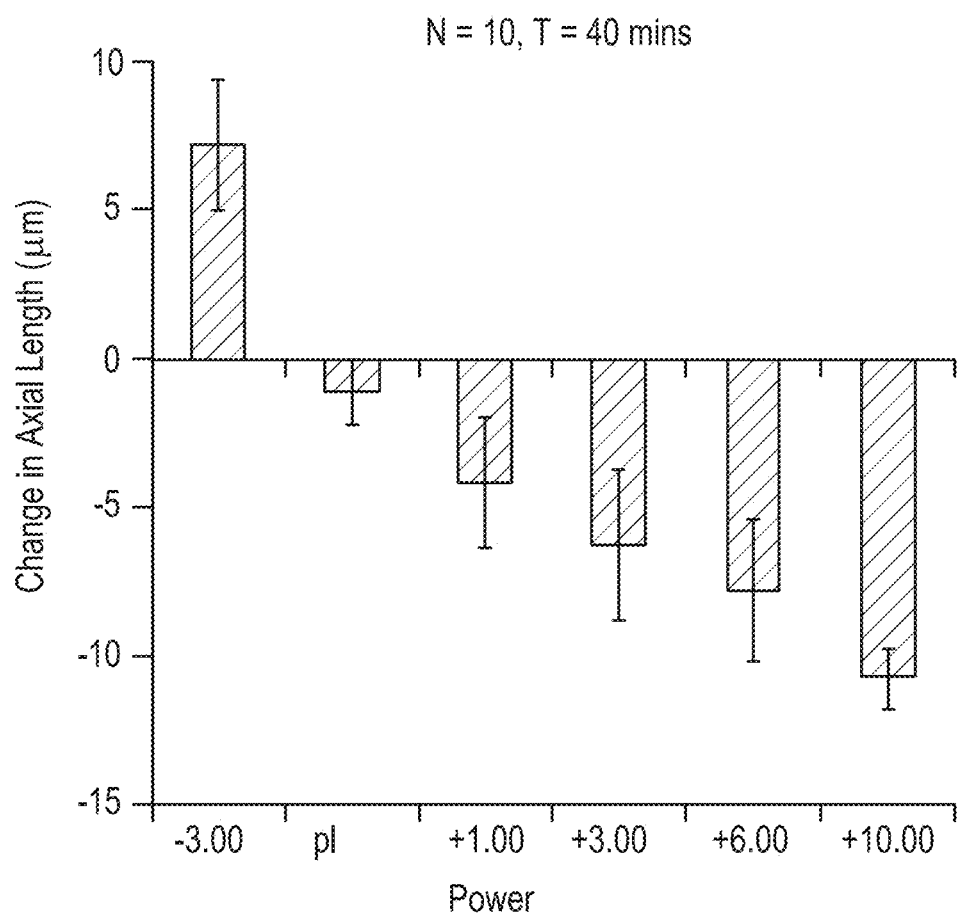

PULSED PLUS LENS DESIGNS FOR MYOPIA CONTROL, ENHANCED DEPTH OF FOCUS AND PRESBYOPIA CORRECTION

CROSS-REFERENCE TO RELATED APPLICATIONS

This application claims the benefit of U.S. Provisional Patent Application No. 62/311,485 filed Mar. 22, 2016.

BACKGROUND OF THE INVENTION

1. Field of the Invention

The present invention relates to ophthalmic lenses, and more particularly, contact lenses designed to slow, retard or prevent myopia progression, to enhance the depth of focus of the eye or to provide a presbyopia correction. The ophthalmic lenses of the present invention utilize transmissive high speed tunable optics to display short periods (pulses) of altered optical powers or optical designs to the human eye, to provide a stop signal to eye growth or to enhance the depth of focus of the eye. Examples of such transmissive high speed tunable optics include a transmissive spatial light modulator (liquid crystal) or variable electrostatic liquid optics, such as an oil/water enclosed lens.

2. Discussion of the Related Art

Common conditions which lead to reduced visual acuity are myopia and hyperopia, for which corrective lenses in the form of spectacles, or rigid or soft contact lenses, are prescribed. The conditions are generally described as the imbalance between the length of the eye and the focus of the optical elements of the eye. Myopic eyes focus in front of the retinal plane and hyperopic eyes focus behind the retinal plane. Myopia typically develops because the axial length of the eye grows to be longer than the focal length of the optical components of the eye, that is, the eye grows too long. Hyperopia typically develops because the axial length of the eye is too short compared with the focal length of the optical components of the eye, that is, the eye does not grow enough.

As noted, myopia typically occurs due to excessive axial growth or elongation of the eye. It is now generally accepted, primarily from animal research, that axial eye growth can be influenced by the quality and focus of the retinal image. Experiments performed on a range of different animal species, utilizing a number of different experimental paradigms, have illustrated that altering retinal image quality can lead to consistent and predictable changes in eye growth.

Furthermore, defocusing the retinal image in both chick and primate animal models, through positive lenses (myopic defocus) or negative lenses (hyperopic defocus), is known to lead to predictable (in terms of both direction and magnitude) changes in eye growth, consistent with the eyes growing to compensate for the imposed defocus. The changes in eye length associated with optical blur have been shown to be modulated by changes in both scleral growth and choroidal thickness. Blur with positive lenses, which leads to myopic blur and decreases scleral growth rate, results in hyperopic refractive errors. Blur with negative lenses, which leads to hyperopic blur and increases scleral growth rate, results in myopic refractive errors. These eye growth changes in response to retinal image defocus have been demonstrated to be largely mediated through local retinal mechanisms, as eye length changes still occur when the optic nerve is damaged, and imposing defocus on local retinal regions has been shown to result in altered eye growth localized to that specific retinal region.

In humans there is both indirect and direct evidence that supports the notion that retinal image quality can influence eye growth. A variety of different ocular conditions, all of which lead to a disruption in form vision, such as ptosis, congenital cataract, corneal opacity, vitreous hemorrhage and other ocular diseases, have been found to be associated with abnormal eye growth in young humans, which suggests that relatively large alterations in retinal image quality do influence eye growth in human subjects. The influence of more subtle retinal image changes on eye growth in humans has also been hypothesized based on optical errors in the human focusing system during near work that may provide a stimulus for eye growth and myopia development in humans. Myopia has a high prevalence rate in many regions of the world. Of greatest concern with this condition is its possible continued progression to high myopia, for example greater than five (5) or six (6) diopters, which dramatically affects one's ability to function without optical aids. High myopia is also associated with an increased risk of retinal disease, cataracts, and glaucoma.

Corrective ophthalmic lenses are used to alter the gross focus of the eye to render a clearer image at the retinal plane, by shifting the focus from in front of the retinal plane to correct myopia, or from behind the retinal plane to correct hyperopia, respectively. However, the corrective approach to these conditions does not address the cause of the condition, but rather is merely prosthetic and only addresses the symptoms. Many approaches for slowing myopia progression rely on the introduction of additional positive power in some region of the lens, such as a concentric bifocal and/or multifocal contact lens. For instance, in US published Patent Application US20160054588, which is owned by applicant and hereby incorporated by reference, the lens contains a center zone with negative power for myopic vision correction, which is surrounded by a treatment zone that has a power profile that increases from the outer margin of the center zone into the treatment zone up to a power of plus 5 diopters. This additional positive optical power in the treatment zone provides the signal to slow eye growth; while the center zone with negative power provides for myopic vision correction. For good vision the lens must also provide optimal correction for distance (far) vision in some region of the lens. In a simple example, a two-zone concentric bifocal design may have a central distance refractive correction and an outer concentric zone of additional positive power that aims to slow eye growth. An optical design such as this does somewhat diminish visual acuity and contrast sensitivity, since not all light that passes through the wearer's entrance pupil will be in focus at the same focal distance (or plane) within the eye.

Another approach considers the response of the eye to the spectral distribution of light. In U.S. Pat. No. 5,838,419 optical filters or tints are utilized on ocular devices in order to shift the spectral distribution of light entering the eye upon the retina. Specifically correction of myopia is achieved by the use of blue filters which shift the spectral distribution towards the short visible wavelengths. Likewise, red filters can be used to treat hyperopia. While this approach may be useful for refractive correction, it falls short of addressing myopia progression.

Ocular devices such as spectacles with light sources to provide a therapeutic effect have also been suggested, as in US published Patent Application US20090192437, which describes a wearable ocular photo-activator device. This device is worn by a subject similar to how spectacles are worn, and the device has a light source capable of being directed towards the eye while the device is worn. Both the power and the wavelength of the light can be adjusted. This is typically done in combination with a photoactive therapeutic agents which are activated by the light source. (ie: phototherapy appears to be the focus of this patent application). Although the inventors of this application state that light can be administered alone for therapeutic purposes, no additional description or the method of treatment is provided. The inventors go on to speak to the benefit of exposing the cornea of the eye to the light of a particular wavelength for a time longer than is convenient for the subject to remain still, (eg: >10 seconds, >20 seconds, . . . > than 2 minutes). This is presumably for the subject to be treated while wearing the glasses and performing other functions rather than the alternative of siting still at a piece of equipment while light is directed to the eye. They also indicate that the light can be "pulsed" and explain that this can be advantageous because the pulsed peak power is higher than the average power during continuous exposure. No mention of myopia treatment is disclosed, the focus of the modulation is wavelength achieved with an artificial light source, and there use of the term "power" in their application is directed to intensity, not diopters. Nor do the inventors address the frequency and duration of the light therapy, but rather focus on photoactive therapeutic agents.

In U.S. Pat. No. 8,764,185, an eye mountable device with a light source directed towards the retina wherein the light source coupled with circuitry is configured to be modulated is disclosed. Modulation can be of the form of color, brightness, intensity, or duration, however in this case the purpose is to send a message to the wearer. The inventors of the '185 patent disclose one form of modulation being providing a series of light pulses such as morse code, in effect achieving the purpose of communicating with the wearer, the key being the pulsing is both understandable and discernable by the wearer of the device. A key aspect of the '185 patent and similar art as a group is that the light source is artificial and included as part of the device itself, this is in contrast with applicant's invention which utilizes incident light passing through the lens, and thus does not require an artificial light source, although an artificial light source can be leveraged if so desired in applicant's invention. Furthermore, the intent in the '185 patent is for the wearer to fully perceive the pulses and to understand the underlying message be it through Morse code as disclosed by the inventors, or other suitable means. This is contrary to applicants invention, and thus teaches away. In accordance with applicant's invention, the pulsing of light, at a frequency high enough not to be perceived by the brain (above the critical flicker fusion rate), but adequate to be perceived by the retina and having a proper focus/power is vital for an effective treatment, and to applicant's knowledge is novel and is in direct opposition of the use of pulsed light as perceivable communication means to the wearer.

In U.S. Pat. No. 9,289,623, owned by applicant and hereby incorporated by reference, an energized ophthalmic device in the form of a contact lens utilizes a light source to treat the symptoms associated with seasonal affective disorder. The use of "intelligent light therapy" is disclosed, meaning that the presence of a processor allows data analysis which can then be used to make adjustments to the light therapy schedule or function, such as frequency, duration, wavelength, exposure time, dioptic power, and intensity to name a few.

In U.S. Pat. No. 4,279,474, a glass spectacle lens utilizes a liquid crystal layer between the two glass portions to make up the spectacle lens. The purpose in the '474 patent was to limit light levels transmitted through the spectacle lens above a specified limit. (ie: Liquid Crystal sunglasses). The inventors of the '474 patent disclose that the use of a liquid crystal layer results in a faster response time than photochromic technology alone and therefore would be preferable not only for their decreased response time but also able to achieve a quicker recovery back to the original state when one returns indoors. Although the inventors of the '474 patent state that an additional object of their invention is to provide a therapeutic lens having continuously variable controlled density, little to no additional information is provided in their specification. No mention of modulation of dioptic power is present, nor is any discussion of controlling the progression of myopia present.

The use of liquid crystals incorporated in contact lenses is a fairly recent innovation. In U.S. Pat. No. 8,542,325 a supply of liquid crystal, in this case thermographic liquid crystals, are utilized to change the color of a contact lens, activated by a change in temperature. In U.S. Pat. No. 9,155,614, an electro-active element is embedded within a flexible refractive optic. By combining flexible conductive materials and liquid crystal, an alterable refractive index is possible, allowing one to correct for refractive errors of the eye.

In U.S. Pat. No. 8,906,088, owned by applicant, and hereby incorporated by reference, a variable focus ophthalmic device including liquid crystal elements and combined with an energy source are used to electrically control refractive characteristics. A liquid crystal lens may provide an electrically variable index of refraction to polarized light incident upon its body. A combination of two lenses where the axis of polarization is rotated in the second lens relative to the first lens allows for a lens element that may be able to vary the index of refraction to ambient non-polarized light. By combining electrically active liquid crystal layers with electrodes, a physical entity may be achieved that may be controlled by applying an electrical field across the electrodes. If there is a dielectric layer that is present on the periphery of the liquid crystal layer then the field across the dielectric layer and the field across the liquid crystal layer may combine into the field across the electrodes. In a three dimensional shape the nature of the combination of the fields across the layers may be estimated based on electrodynamic principals and the geometry of the dielectric layer and the liquid crystal layer. If the effective electrical thickness of the dielectric layer is made in a non-uniform manner then the effect of a field across the electrodes may be "shaped" by the effective shape of the dielectric and create dimensionally shaped changes in refractive index in the liquid crystal layers. In some exemplary embodiments, such shaping may result in lenses that have the ability to adopt variable focal characteristics. An alternative exemplary embodiment may derive when the physical lens elements that contain the liquid crystal layers are shaped themselves to have different focal characteristics. The electrically variable index of refraction of a liquid crystal layer may then be used to introduce changes in focal characteristics of the lens based on the application of an electric field across the liquid crystal layer through the use of electrodes. The shape that the front containment surface makes with the liquid crystal layer and the shape that the back containment surface makes with the liquid crystal layer may determine to first order the focal characteristics of the system.

Clearly the sophistication and utilization of components such as liquid crystals, circuitry and energy sources has recently and significantly expanded the potential application of energized or powered ophthalmic products, that can now perform a variety of tasks.

U.S. Pat. No. 6,511,175 is directed to the treatment of amblyopia in children, also known as "lazy eye". In the '175 patent, goggles or glasses are fitted with liquid crystal lenses that are selectively made opaque for the lens over the strong eye, in order to force the child wearer to exercise the weak eye. The '175 patent discloses the use of a variable frequency pulse generator to time the LCD lens transitions from the transparent to the opaque state. They also disclose the frequency of these transitions being above the flicker fusion rate which they identify to be generally about 60 Hz. It is important to note that the flicker fusion threshold is a statistical rather than an absolute quantity, and can vary with wavelength, brightness or illumination. It can also be different depending on where the illumination occurs within the retina, as well as be affected by the fatigue of the individual. Although applicant's invention also relies on leveraging a frequency above the flicker fusion rate, applicants invention is modulating dioptic power, that is to say, altering focus and defocus of the transmitted image at a frequency above the flicker fusion rate to treat myopia progression. Inventors of the '175 patent are modulating the passage of entire transmitted image through the lens, by alternating between occluding or blocking the transmitted image with that of transmitting the image through the lens in order to treat amblyopia. Applicant's invention is different and distinct from the '175 patent because in accordance with applicant's invention, the image is continually transmitted through the lens but the image or image quality alternates between the focus and defocus states, as it is the presence of the defocus state that sends the signal to temper eye growth.

In a recent research article published on Sep. 15, 2016 (Papadatou et. al. "Temporal Multiplexing with Adaptive Optics for Simultaneous Vision" Biomedical Optics Express Vol. 7, No. 10 (October 2016).), the researchers indicated that while simultaneous vision with temporal multiplexing can be achieved artificially with high-speed optoelectronic devices, they also go on to say that the practical use is limited. The authors indicated that due to size and weight considerations as well as the need for a power supply, such use is best limited to testing visual performance.

In U.S. Pat. No. 7,423,801, the inventors disclose a multifocal lens with a transparent optoelectronic focal modulation device which comprises liquid crystal cells, encapsulated within the lens body, whose purpose is to switch between two or more focal states, a near-focus state and a distant focus state in contrast to more conventional multifocal lenses which focus both near and far objects onto the retina simultaneously. While the '801 patent discloses two focus states (ie: near and distance) it does not consider an intentional defocus for controlling myopia progression.

While many of the previously discussed designs are extremely sophisticated, they do not envision artificially and purposefully using a control system and liquid crystals to temporally modulate the transmitted retinal image in order to effectively treat the progression of myopia while minimizing the impact to the viewed image. Accordingly, there exists a need for a lens design that is capable of slowing myopia progression that does not appreciably diminish visual acuity and contrast sensitivity compared to conventional optical designs.

SUMMARY OF THE INVENTION

The present invention provides a pulsed plus lens design for myopia control, enhanced depth of focus and presbyopia correction that overcomes the limitations of the prior art as briefly set forth above. In accordance with the present invention by temporally modulating the transmitted retinal image, or a portion thereof, in terms of power/focus in order to achieve a fleeting temporal defocus imperceptible to the brain, over a duration that is therapeutically effective to the retina, one can mitigate further progression of myopia by having an effect on eye growth.

In accordance with one aspect, the present invention is directed to an ophthalmic lens system. The ophthalmic lens system including means for electronically oscillating the focus of incoming light upon the retina wherein the focus is temporally modulated at a level that is imperceptible to a wearer of the lens while providing acceptable vision at both near and far viewing distances. The ophthalmic lens system comprising a first lens, a variable focus optic within the lens, the variable focus optic is capable of being tuned, a controller to control the variable focus optic having a selectable duty cycle, and a power supply for the variable focus optic and the controller. Optionally the system may contain an artificial light source as well.

The ophthalmic lenses of the present invention utilize transmissive high speed tunable optics to display short periods (pulses) of altered optical powers or optical designs to the human eye, these short periods or pulses have the effect of providing a stop signal to eye growth (myopia progression mitigation) and/or to enhance the depth of focus of the eye. Examples of such transmissive high speed tunable optics include a transmissive spatial light modulator (liquid crystal) or variable electrostatic liquid optics, such as an oil/water enclosed lens.

The ophthalmic lens includes, within its primary optical zone, transmissive high speed tunable optics which is electronically addressed and programmable. While providing optimal distance correction, the high speed tunable optics in accordance with the present invention also induces imperceptible pulsed plus powers to create a myopic defocus in front of the retina temporally. Key principles to consider in order to be effective in controlling Myopia, while still providing satisfactory vision, include ensuring adequate distance vision generally 20/25 or better, with minimal objectionable image artifacts. Additionally, to control the further progression of myopia, the quality of the image in front of the retina must always be superior to the quality of the image behind the retina when viewing an object at any distance and at every pupil size. Lastly, the quality of the image on the retina must always be superior to the quality of the image either in front of or behind the retina.

To ensure a therapeutic effect, the ratio of the period of plus power to that of optimal distance correction ranges from about five to ninety percent. The ratio of different powers may also be defined by the duty cycle, which is the ratio of the period of plus power displayed in a unit period of time. For example, displaying plus power for a total 100 ms in any 1 second of total period is a duty cycle of 10 percent. This is true if the 100 ms portion is continuous and occurs once every second, or intermittent occurring several times during the 1 second period, as long as the cumulative duration is 100 ms during the 1 second period. In either case, both situations have a similar duty cycle of 10 percent and both can be therapeutically effective, however in accordance with the present invention, applicants have found that in a given duty cycle, with intermittent pulsing, the negative impact to the viewed image can be minimized. Alternatively, the presence of a controller allows one to also modulate wavelength and intensity in a similar fashion. Each of these approaches may also have a therapeutic effect.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 2 is a representation of the two equivalent but differing duty cycles of the pulse display method resulting in a 10% duty cycle in accordance with the present invention.

FIG. 6 shows the change in length of the eye relative to a range of dioptric powers.

DETAILED DESCRIPTION OF THE PREFERRED EMBODIMENTS

Figure 1:
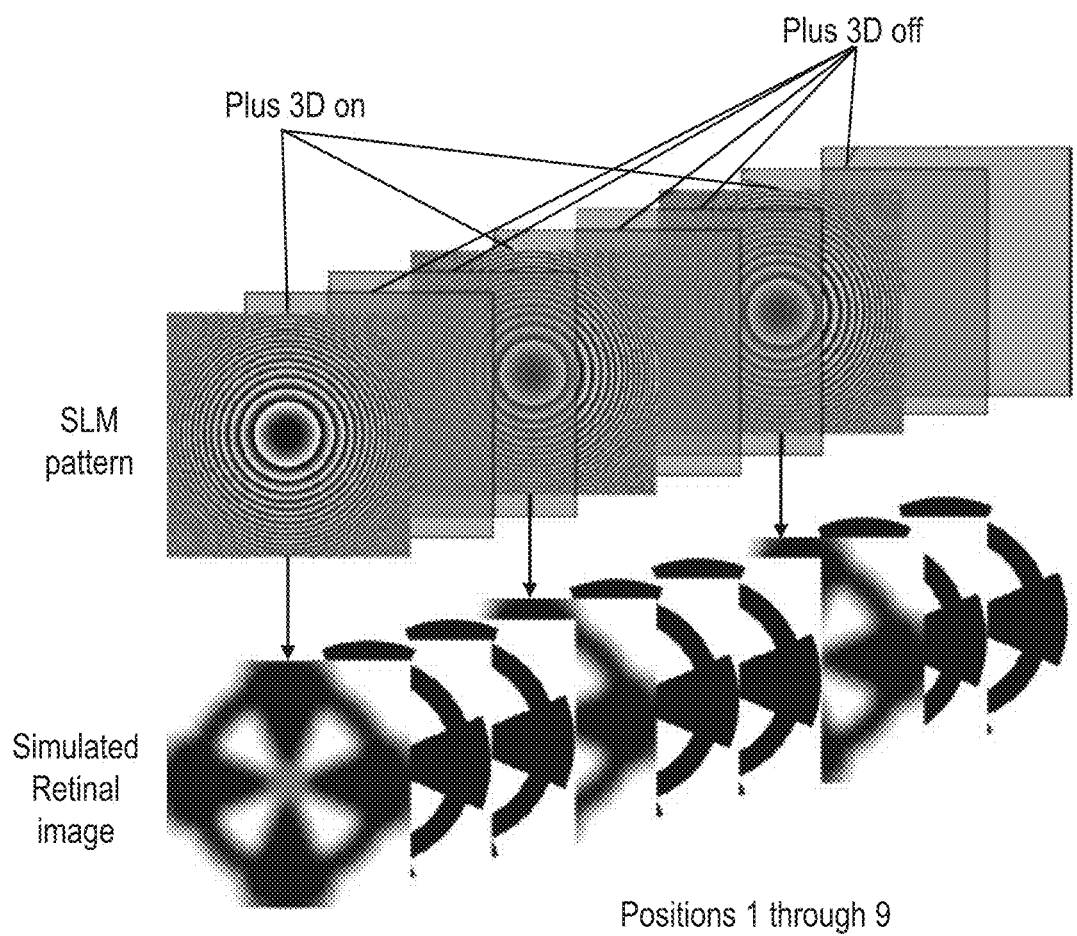
FIG. 1 is a diagrammatic representation of the pulsed plus display method with plus power and plano power alternatively displayed by the transmissive high speed tunable optics in accordance with the present invention.

As electronic devices continue to be miniaturized, it is becoming increasingly more likely to create wearable or embeddable microelectronic devices for a variety of uses. Such uses may include monitoring aspects of body chemistry, administering controlled dosages of medications or therapeutic agents via various mechanisms, including automatically, in response to measurements, or in response to external control signals, and augmenting the performance of organs or tissues. Examples of such devices include glucose infusion pumps, pacemakers, defibrillators, ventricular assist devices and neuro-stimulators. A new, particularly useful field of application is in ophthalmic lenses, including wearable lenses such as spectacles and contact lenses as well as implantable lenses such as onlays, inlays and intraocular lens (IOL'S). For example, a wearable lens may incorporate a lens assembly having an electronically adjustable focus to augment or enhance performance of the eye. Such an electronic variable-focus lens, for example one utilizing liquid crystal or liquid meniscus technology, may require sufficient activation voltage to affect a change in optical power. Depending on design parameters, such a lens may also have inherent capacitance, which must be charged and discharged. Thus, in order to alternate focus faster than the flicker threshold, electronic driver circuitry must sink and source current fast enough to toggle the lens between the voltages associated with near and far focus given the capacitance of the lens. Numerous techniques may be considered to satisfy these criteria, including those mentioned in U.S. Pat. No. 9,351,827 owned by applicant and hereby incorporated by reference.

In this example the electronic components can be encapsulated/embedded in the lens body which is adapted to fit on the surface of the cornea of the eye as a contact lens. In an alternate example, the lens body with the embedded electronic components can be adapted by the addition of integrated haptics with the lens body and be implanted as an Intraocular lens. In another example, either with or without adjustable focus, a wearable contact lens may incorporate electronic sensors to detect concentrations of particular chemicals in the precorneal (tear) film. The use of embedded electronics in a lens assembly introduces a potential requirement for communication with the electronics, for a method of powering and/or re-energizing the electronics including power control or power management circuitry, for interconnecting the electronics, for internal and external sensing and/or monitoring, and for control of the electronics and the overall function of the lens.

Conventional contact lenses are polymeric structures with specific shapes placed on eye to correct various vision problems as briefly set forth above. Conventional spectacle lenses typically comprise polymeric structures with specific shapes to correct various vision problems as briefly set forth above and are secured in place by frames. Conventional intraocular lens are polymeric structures with integrated haptics to secure the lens inside the lens capsule after removal of the human crystalline lens. To achieve enhanced functionality, various circuits and components have to be integrated into these polymeric structures and/or frames. For example, control circuits, microprocessors, communication devices, power supplies, sensors, actuators, light emitting diodes, and miniature antennas may be integrated into contact lenses or intraocular lenses via custom built optoelectronic components to not only correct vision, but to enhance vision as well as provide additional functionality as is explained herein. In addition, spatial light modulators, as explained in greater detail subsequently, may also be incorporated into the ophthalmic lenses. Electronic and/or powered contact lenses, intraocular lenses or spectacles may be designed to provide enhanced vision via zoom-in and zoom-out capabilities or just simply modifying the refractive capabilities of the lenses. Electronic and/or powered contact lenses, intraocular lenses and/or spectacles may be designed to enhance color and resolution, to display textural information, to translate speech into captions in real time, to offer visual cues from a navigation system, to provide image processing and even internet access.

The lenses may be designed to allow the wearer to see in low light conditions. The properly designed electronics and/or arrangement of electronics on lenses may allow for projecting an image onto the retina, for example, without a variable focus optic lens, provide novelty image displays and even provide wakeup alerts. Alternately, or in addition to any of these functions or similar functions, the contact lenses, intraocular lenses and/or spectacles may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured ophthalmic lens may incorporate sensors for monitoring cholesterol, sodium and potassium levels as well as other biological markers. This coupled with a wireless data transmitter could allow a physician to have almost immediate access to a patient's blood chemistry without the need for the patient to waste time getting to a laboratory and having blood drawn. In addition, sensors built into the ophthalmic lenses may be utilized to detect light incident on the eye to compensate for ambient light conditions or for use in determining blink patterns.

Figure 8:
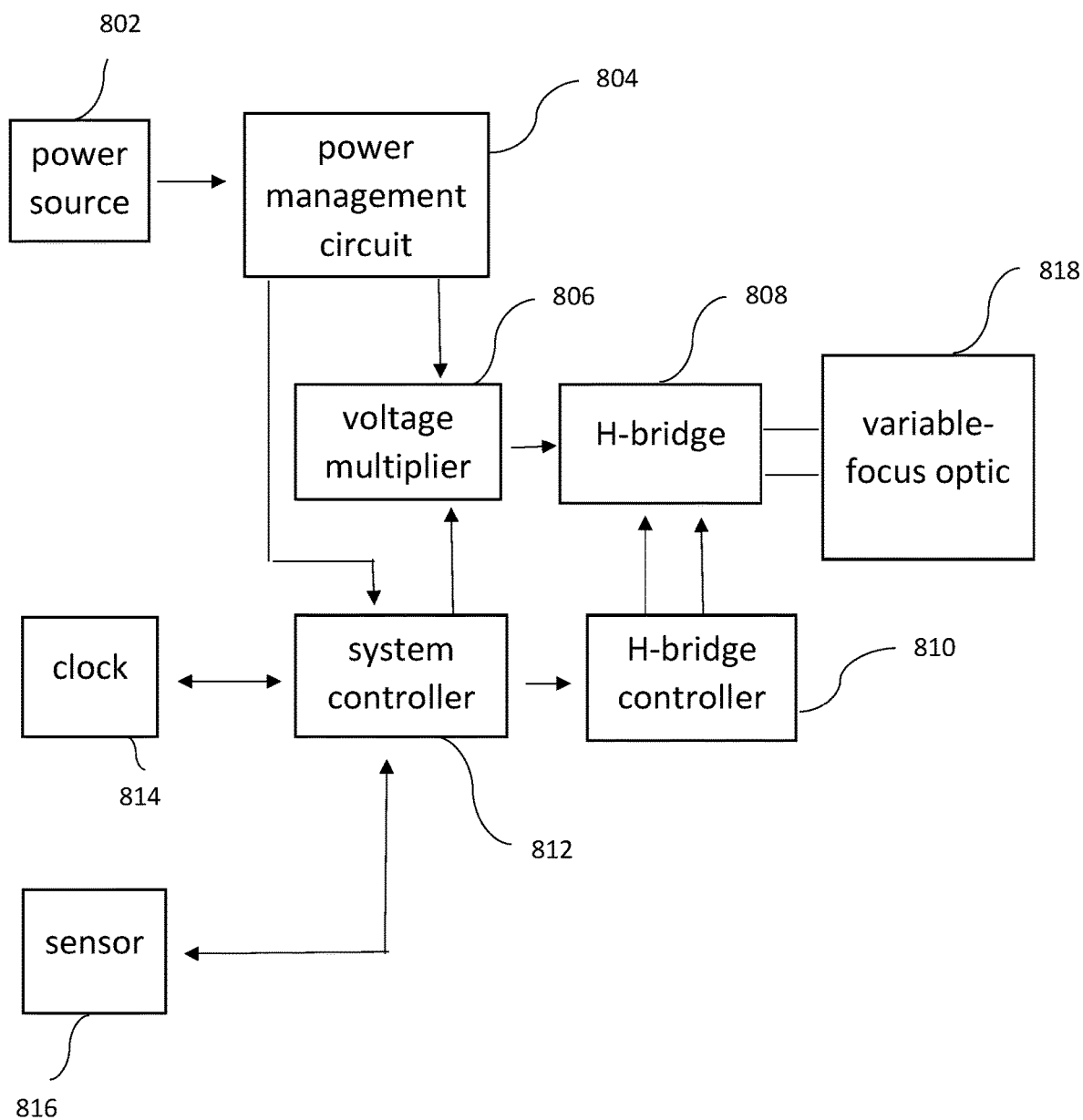
FIG. 8 is a block diagram of an ophthalmic lens in accordance with the present invention.

The present invention is directed to a powered ophthalmic lens comprising an electronic system, which may actuate implement a variable-focus lens or any other device or devices configured to implement any number of numerous functions that may be performed, for example, a spatial light modulator to be used in the slowing of myopia progression. The electronic system includes one or more batteries or other power sources, power management circuitry, one or more sensors, clock generation circuitry, control circuitry implementing suitable control algorithms, and lens driver circuitry. FIG. 8 is a block diagram of an ophthalmic lens 800 including a power source 802, power management circuitry 804, lens driver circuitry 806, 808, 810, a system controller 812, clock 814, sensor 816 and variable focus optic 818. The complexity of these components may vary depending on the required or desired functionality of the ophthalmic lens. It is important to note that the lens designs of the present invention may be incorporated into any number of different ophthalmic lenses formed from any number of materials. Specifically, the lens design of the present invention may be utilized in any of the contact lenses described herein, including, daily wear soft contact lenses, rigid gas permeable contact lenses, bifocal contact lenses, toric contact lenses and hybrid contact lenses. In addition, although the invention is described primarily with respect to contact lenses, it is important to note that the concept of the present invention may be utilized in spectacle lenses, intraocular lenses, corneal inlays and onlays.

The flicker fusion threshold (or flicker fusion rate) is a concept in the psychophysics of vision. In the late 1800's and early 1900's Ferry and Porter found that the frequency up to which Flicker can be observed increase linearly with the logarithm of the luminance. This is known as the Feery-Porter law. This frequency is called the critical flicker frequency. It is defined as the frequency at which an intermittent (flickering) light stimulus appears to be completely steady to the average human observer. As an example, this principle is present in the choice of a frame rate of 72 Hertz for computer displays, which is sufficient to avoid flicker completely. As long as the modulation frequency is kept above the flicker fusion threshold, the perceived intensity may be changed by changing the relative periods of light and darkness. For example, if the dark periods are prolonged it will darken the image (Talbot-Plateau law).

In accordance with the present invention, the same flicker fusion principle may also be applied to optical power. By using transmissive high speed tunable optics, the optical power of the lens may be rapidly changed at a frequency that is above the flicker fusion threshold. The effective optical characteristics of the ophthalmic lens may be changed by varying the relative periods of display of various optical powers or designs. For example, a transmissive high speed tunable optic could display two simple powers (plano and +3 Diopters "D") by rapidly switching the power between plano and +3D, as shown in FIG. 1. Provided the modulation frequency is kept above the flicker fusion threshold, then the impact of the two powers on visual acuity for example, is determined by the ratio of plano to +3D display time (i.e. the duty cycle). Transmissive high speed tunable optics may therefore produce the equivalent of having two or more optical powers/designs focusing light into the eye at the same time (similar to bifocal or multifocal contact lenses). This would equate to one for vision correction and the other for myopia progression mitigation, but with the result of not having the ability to perceive any compromise in vision quality as the later for myopia progression mitigation is of limited duration or duty cycle at a frequency above the flicker fusion threshold in accordance with the present invention.

The ophthalmic lens includes, within its primary optical zone, transmissive high speed tunable optics which is electronically addressed and programmable. While providing optimal distance correction, the high speed tunable optics also induces extremely short intermittent plus powers to create myopic defocus in front of the retina. This is accomplished in a pulsed method in accordance with the present invention. The ratio of the period of plus power and optimal distance correction ranges from about 5 to 90 percent. The ratio of different powers may also be defined by the duty cycle, which is the ratio of period of plus power displayed in a unit period of time. For example, displaying plus power for 100 ms in any 1 second of total period is a duty cycle of 10 percent whether that is accomplished with a single occurrence of 100 ms in duration every second, four occurrences each 25 ms in duration every second, or ten occurrences each being 10 ms in duration every second. Regardless of the scenario utilized each of these scenarios represents a duty cycle of 10 percent. While the duty cycle can remain constant or in some situations can be varied as the therapy may require, the scenario used over the course of the wear period is important as some variations while therapeutically effective, may also be visually perceived. Having an adequate duty cycle for effective treatment and short enough periods of plus power to remain imperceptible is vital to optimally correct one's vision while providing a therapy for controlling myopia progression. While a duty cycle of approximately 5 percent or more is preferred, as this is least disruptive to both visual acuity and contrast sensitivity, other values between 5 and 90 percent may be utilized.

The plus power induced by the tunable optics for myopia control may vary from +1.0D to +20D. On the other hand, the power induced by the tunable optics for presbyopia correction can vary from −4D to +4D. However, the optical designs induced are not limited to single spherical power. Optical designs including multifocal lenses, progressive lenses and other optical designs may also be applied. The displayed optical design may also vary as a function of time, or dependent on the light level at the subject's pupil, or the subject's pupil size. The induced power pattern does not necessary cover the whole optical zone and could be limited to zones/portions within the pupil. For myopia, typically pupil size ranges from 4 to 8 mm in mesopic conditions. Furthermore, for optimum vision, the central 2 mm of the lens optical zone can be free of the induced pulsed myopic defocus, leaving a fixed primary distance correction. It is important to note that as the entrance pupil size of the eye varies among subpopulations, in certain exemplary embodiments, the lens design may be customized to achieve both good foveal vision correction and myopic treatment efficacy based on the patient's average pupil size. Moreover, as pupil size correlates with refraction and age for pediatric patients, in certain exemplary embodiments, the lens may be further optimized towards subgroups of the pediatric subpopulation of a specific age and/or refraction based upon their pupil sizes.

Pulse Plus Display by Transmission High Speed Tunable Optics

The high speed tunable optics covering the optical zone of the ophthalmic lenses is used to induce imperceptible short pulses of plus power to the eye along with periods of optimal distance correction. In the example shown in FIG. 1, the high speed tunable optics displays a series of wavefront patterns of both plus power (+3D) and plano wavefront patterns to the eye. In this example, the plus power wavefront patterns are transmitted as designated in positions 1, 4 & 7 (indicated by the term "Plus 3D on") while the plano wavefront patterns are transmitted as designated in positions 2, 3, 5, 6, 8 & 9 (indicated by the term "Plus 3D off") in accordance with the present invention. As long as the pulse display is performed with a modulation frequency higher than the flicker fusion rate, the eye observes a stable image. As a result it is less blurred than viewing through a static power of +3D alone, while still providing the therapeutic effect of myopia control or progression mitigation achieved by the presence of an intermittent yet imperceptible plus power image.

Duty Cycle of the Pulse Display Method

How the target image appears to the eye is dependent on the amount of plus power induced, and also dependent on the duty cycle of pulse display. A duty cycle is defined as the percentage of one period in which a signal is active. The two examples (conditions) of duty cycle shown in FIG. 2 are two pulse plus display conditions, both having a 10 percent duty cycle when +3D power is activated. The first, utilizes four (4) distinct 25 ms periods of induced plus power The eye is exposed to the same total period of 100 ms of plus power in every one second period in both conditions. In condition 1, the modulation frequency is 40 Hz, which is higher than the average flicker fusion threshold in the human eye and thus flicker or image instability will not be present. The eye will observe a slightly blurred but steady image. In condition 2, (a single 100 ms period every second) the modulation frequency is 10 Hz which is lower than the flicker fusion threshold in the human eye. In this second condition the eye will observe noticeable jitters when the displayed wavefront patterns switch from +3D to plano. Thus while both situations can be effective in treating myopia progression, condition 1 may be more visually comfortable than condition 2 to some individuals. Multiple other combinations, each having a duty cycle of 10% exist, some additional examples are shown in the table below:

TABLE 1

| Condition or Example | Duty Cycle | # of sub-periods/second | Duration of sub-period (ms) |
| --- | --- | --- | --- |
| 1 (40 hz) | 10% | 4 | 25 ms |
| 2 (10 Hz) | 10% | 1 | 100 ms |
| 3 (50 Hz) | 10% | 5 | 20 ms |
| 4 (100 Hz) | 10% | 10 | 10 ms |
| 5 (25 hz) | 10% | 2.5 | 40 ms |

Figure 3A:
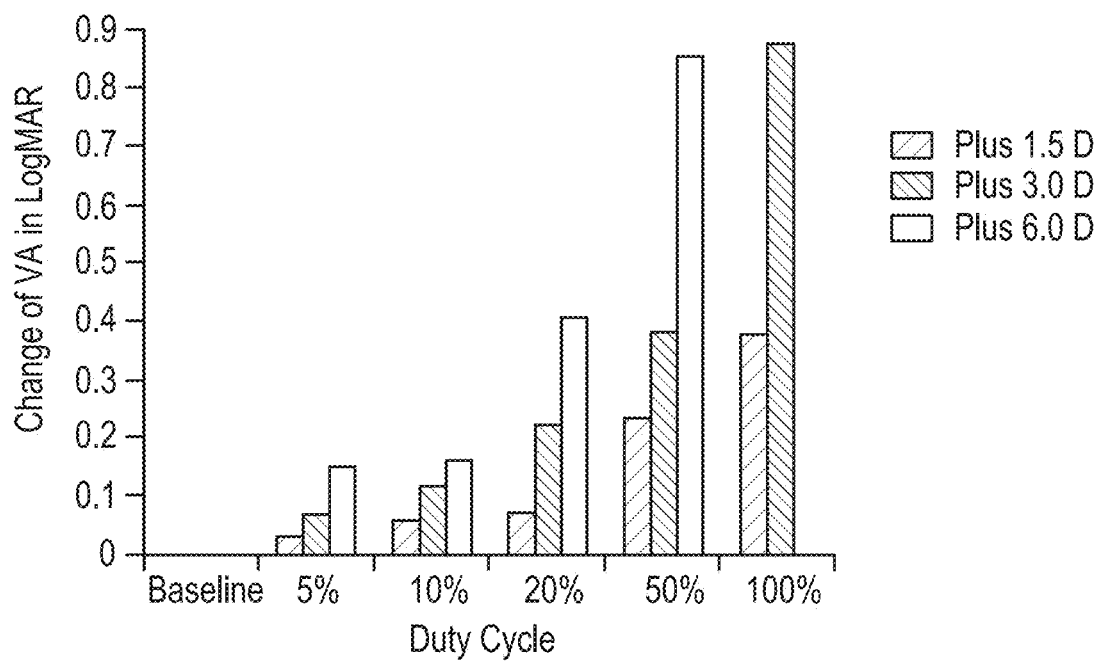
FIGS. 3A and 3B are graphical representations of the impact of pulsed display of plus power of +3D on vision performance, with the change of VA in Log MAR versus duty cycle illustrated in FIG. 3A and with the change of Weber contrast versus duty cycle illustrated in FIG. 3B in accordance with the present invention.
Figure 3B:
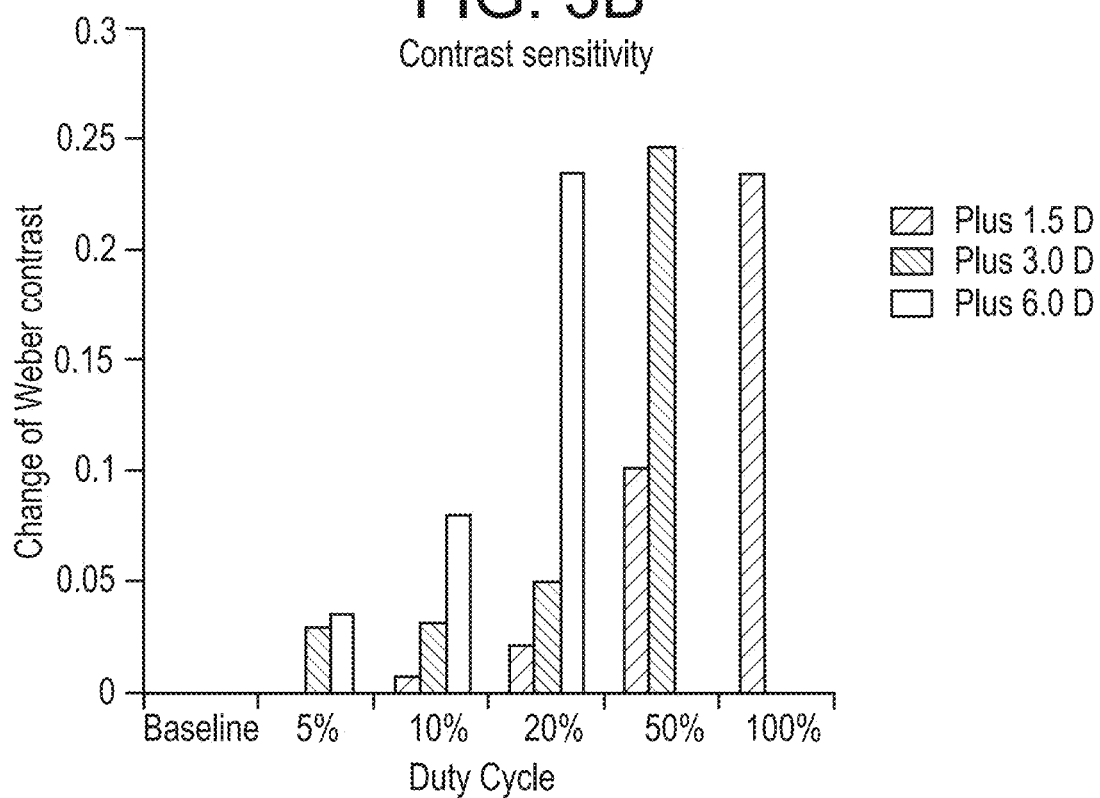

Both visual acuity and contrast sensitivity decrease as the induced plus power and duty cycle increase. The visual acuity and Weber contrast sensitivity for the above pulsed plus conditions relative to a best spherical correction and in comparison to a conventional +3D sphere lens is summarized in Table 2 below. FIGS. 3A and 3B graphically illustrate the results of Table 2. The values in both table 2 and the charts of FIGS. 3A and 3B clearly indicate that either increasing duty cycle or increasing dioptric power results in and is proportional to both the loss of visual acuity and loss of contrast sensitivity. It should also be noted that increasing duty cycle or increasing dioptric power is proportional to therapeutic effectiveness. Thus one needs to increase duty cycle or dioptric power to the point where it is therapeutically effective, but not to the point where the loss of visual acuity or contrast sensitivity is excessive. In accordance with the present invention, applicants have determined the proper balance of duty cycle, dioptric power and modulation frequency with that of myopia progression effectiveness to achieve acceptable visual performance as measured by visual acuity and contrast sensitivity. These two indicators of visual performance are somewhat subjective amongst patients and as such may differ from patient to patient.

As stated previously Myopia typically develops because the axial length of the eye grows too long, likewise a reduction in change in axial length can be used as a measure for therapeutic effectiveness of treating myopia progression. FIG. 3c shows the impact of power upon the change in axial length in a study of 10 subjects after wearing the lenses of varying power for a period of 40 minutes. In this situation, one can see the impact of both negative and positive power. Whereas the negative power results in a hyperopic defocused retinal image (focal image plane is posterior to the retina) and thus eye receives message to grow and subsequent change in axial length is positive. This is in contrast to a positive power which results in a myopic defocused retinal image (focal image plane is anterior to the retina) and thus the change in axial length of eye is negative. As FIG. 3C shows, increasing plus powers is directly proportional to an increased reduction (ie: negative change) in axial length of the eye. Likewise the duration of how long the power is present (ie: duty cycle) is also proportional to the change in axial length.

TABLE 2

| Plus power induced | Duty cycle | Loss of visual acuity mean | Loss of Weber contrast sensitivity mean |
| --- | --- | --- | --- |
| +1.5D | 5% | 0.033 | 0 |
|  | 10% | 0.059 | 0.007 |
|  | 20% | 0.071 | 0.021 |
|  | 50% | 0.232 | 0.102 |
|  | 100% | 0.376 | 0.234 |
| +3.0D | 5% | 0.07 | 0.029 |
|  | 10% | 0.117 | 0.031 |
|  | 20% | 0.221 | 0.05 |
|  | 50% | 0.379 | 0.246 |
|  | 100% | 0.876 | NA |
| +6.0D | 5% | 0.151 | 0.035 |
|  | 10% | 0.164 | 0.081 |
|  | 20% | 0.404 | 0.235 |
|  | 50% | 0.856 | NA |
|  | 100% | NA | NA |

Control circuits, as stated above, may comprise algorithms which control spatial light modulators to create the flickered pulses. In one exemplary embodiment, the algorithm may utilize image arrays comprising 4, 5 or 10 frames of spatial light modulator files, which corresponds to 100, 125 and 250 ms of spatial light modulator display time. These image arrays can define the usual duty cycles, for example 10 percent, 20 percent, 50 percent and 100 percent as set forth in Table 2 above. In another exemplary embodiment, the algorithm may utilize image arrays comprising 100 frames of spatial light modulator files, which can be utilized to create duty cycles of any ratio, for example, 20 percent, 21 percent, 22 percent and so on. The image array may be pre-loaded into the system memory before display.

Figure 4:
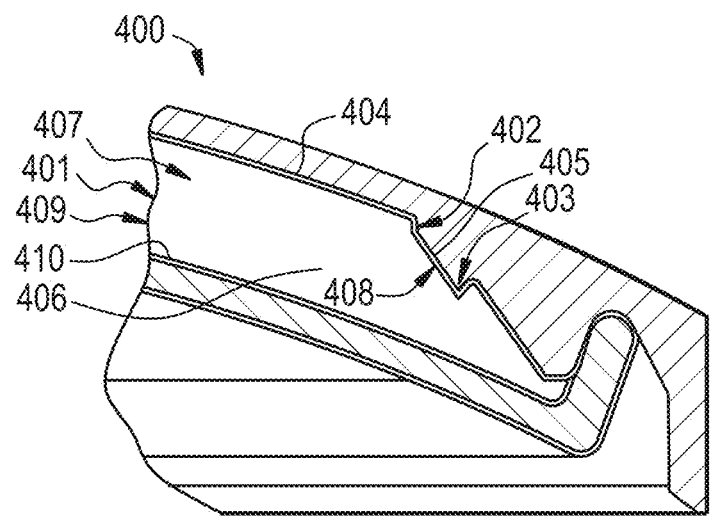
FIG. 4 illustrates a variable optic portion of an arcuate liquid meniscus lens in accordance with the present invention.

Referring now to FIG. 4, a curved liquid meniscus lens 400 is illustrated with a liquid meniscus boundary 401 between the saline solution 406 and oil 407. According to some preferred embodiments, a meniscus wall 405 is defined in the front curve lens 404 by a first angular break in an arcuate wall extending between 402 and 403. The liquid meniscus boundary 401 will move up and down the meniscus wall 405 as charge is applied and removed along one or more conductive coatings or conductive materials 408. In some preferred embodiments, a conductive coating 403 will extend from an area internal to the cavity 409 holding the saline solution 406 and the oil 407 to an area external to the cavity 409 containing the saline solution 406 and oil 407. In such embodiments, the conductive coating 403 may be a conduit of an electrical charge applied to the conductive coating 403 at a point external to the cavity 409 to an area of the conductive coating within the cavity and in contact with the saline solution 406. Generally, a liquid meniscus lens may be viewed as a capacitor with one or more of: conductive coatings, insulator coatings, pathways, and materials are present on or through the front curve lens 404 and back curve lens 410. According to the present invention, a shape of a liquid meniscus boundary 401 and therefore a contact angle between the liquid meniscus boundary 401 and the front curve lens 404 change in response to an electrical charge applied to a surface of at least a portion of one or both of the front curve lens 404 and the back curve lens 410. In accordance with the present invention, a change in an electrical current applied to the saline solution via the conductive coatings or materials changes a position of the liquid meniscus boundary 401 along a meniscus wall 405.

Figure 5:
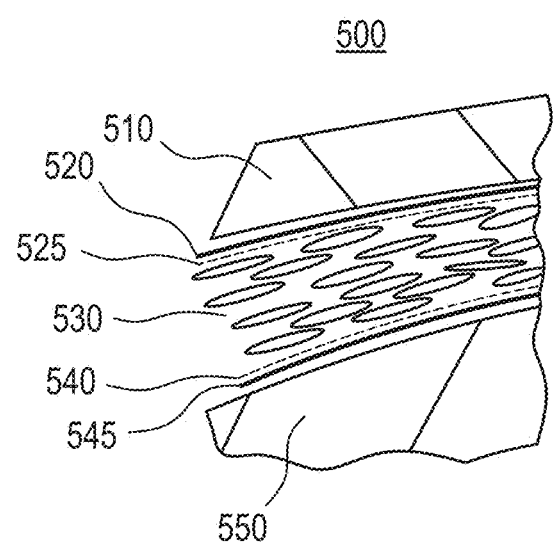
FIG. 5 shows a variable optic portion with a liquid crystal layer in accordance with the present invention.

Referring to FIG. 5, a variable optic portion 500 that may be inserted into an ophthalmic lens is illustrated with a liquid crystal layer 530. The variable optic portion 500 may have a similar diversity of materials and structural relevance as has been discussed in other sections of this specification. In some exemplary embodiments, a transparent electrode 545 may be placed on the first transparent substrate 550. The first lens surface 540 may be comprised of a dielectric film, and in some exemplary embodiments, alignment layers which may be placed upon the first transparent electrode 545. In such exemplary embodiments, the shape of the dielectric layer of the first lens surface 540 may form a regionally varied shape in the dielectric thickness as depicted. Such a regionally varied shape may introduce additional focusing power of the lens element. In some embodiments, for example, the shaped layer may be formed by injection molding upon the first transparent electrode 545 substrate 550 combination. In some exemplary embodiments the first transparent electrode 545 and the second transparent electrode 520 may be shaped in various manners. In some examples, the shaping may result in separate distinct regions being formed that may be energized separately. In other examples, the electrodes may be formed into patterns such as a helix from the center of the lens to the periphery which may apply a variable electric field across the liquid crystal layer 530. In either case, such electrode shaping may be performed in addition to the shaping of dielectric layer upon the electrode or instead of such shaping. The shaping of electrodes in these manners may also introduce additional focusing power of the lens element under operation. A liquid crystal layer 530 may be located between the first transparent electrode 545 and a second transparent electrode 525. The second transparent electrode 525 may be attached to the top substrate layer 510, wherein the device formed from top substrate layer 510 to the bottom substrate layer 550 may comprise the variable optic portion 500 of the ophthalmic lens. Two alignment layers may also be located at 540 and 525 upon the dielectric layer and may surround the liquid crystal layer 525. The alignment layers at 540 and 525 may function to define a resting orientation of the ophthalmic lens. In some exemplary embodiments, the electrode layers 525 and 545 may be in electrical communication with liquid crystal layer 530 and cause a shift in orientation from the resting orientation to at least one energized orientation.

Whether a liquid meniscus approach or a liquid crystal approach is utilized for the variable optic portion, either approach would need to be extremely responsive in order to produce the extremely brief intermittent pulsing.

Transmissive high speed tunable optics to produce two or more optical powers/designs focusing light into the eye by the pulse display method in accordance with the present invention include a number of advantages. The entire transmissive lens can change power to produce the two or more focal planes. If the pulsed displays are spherical powers, this eliminates the need for accurate centration of multifocal contact lenses with respect to the pupil. In spectacle lenses, this overcomes the problem with changes in the line of sight with respect to the spectacle lens multifocal optical design. In myopia control applications, the additional positive power to slow eye growth is presented to full field of the retina and is not restricted to one or more regions of the lens (that project to defined regions of the retina). In extended depth of focus applications for presbyopia, the additional positive power to provide intermediate and near vision is presented to full field of the retina and is not restricted to one or more regions of the lens. Using transmissive high speed tunable optics, the duty cycle can be easily "tuned" based on subjective feedback to produce acceptable vision quality. Using transmissive high speed tunable optics, the duty cycle can be "tuned" based on biomarker feedback that indicates the visual task being undertaken (for example, near work as a trigger for myopia control or presbyopia correction). The transmissive high speed tunable optics may be in the form of simple defocus (e.g. plano and +3DS) or could be in more complex forms such as astigmatism, spherical aberration, multifocals or combinations of any other optical aberrations. The variable focus optic may provide differing degrees of change in focus across the lens. For example, to minimize impact on visual acuity the central portion of the lens may be tuned to undergo no change or less change in the duty cycle*power factor than more peripheral parts of the lens. The more peripheral parts of the lens may undergo larger changes in the duty cycle*power factor since the peripheral retina is less sensitive to blur with respect to visual acuity and it has also been proposed that defocus in the peripheral retina may be impactful in influencing refractive development of the eye. The limitations on the optical design are due to the type of transmissive high speed tunable optics. For example, a transmissive spatial light modulator with multiple individual tunable pixels, can create any complex design based on the size and distribution of the pixels. On the other hand, an electrostatic tunable liquid lens optic would be limited to less complex optical designs(e.g. sphere, astigmatism, spherical aberration). Furthermore, for most individuals, refractive management involves two functioning eyes that may or may not allow full binocular vision. Management of refractive development in accordance with the present invention may vary depending on the relative status of the two eyes. In one embodiment, the variable optic presented to an eye with a greater degree of myopia may be tuned to have a greater duty cycle*power factor, to achieve greater refractive control in that eye, than that in the contralateral eye, which may then be relied on more for visual acuity. In another embodiment, the presentation of the plus power may be varied in time before the eyes, allowing uninterrupted clear vision in at least one eye at any given time, allowing for both optimal visual acuity and maximal myopia treatment effect.

Prospective clinical trials have shown that the rate of myopia progression in humans can be influenced by the optical design of soft contact lenses. These clinical trials have established that the introduction of positive defocus in the retinal image of children slows the progression of myopia. Changes in eye length associated with defocus are modulated by changes in both scleral growth and choroidal thickness, the net effect of which results in an anterior or a posterior movement of the retina toward the image plane. A defocused retinal image, be it a myopic defocused image (ie: focal plane is anterior to the retina) or a hyperopic defocused image (ie: focal plane is posterior to the retina) can mitigate the progression of myopia or hyperopia. Applicants have learned that induced myopic defocus, leads to a thickening of the choroid and to a decreased scleral growth rate (which results in anterior movement of the retina), and induced hyperopic defocus leads to a thinning of the choroid and an increase in scleral growth rate (which results in posterior movement of the retina). Choroidal thickness changes in response to imposed defocus have been observed in both avian and primate animal models, and have been demonstrated to occur rapidly and to precede longer term, sclera-mediated changes in eye size. Research has shown that in young adult human subjects, short-term changes in the choroid thickness and axial length occur in a way similar to that observed in other animal species in response to optical defocus. Studies investigating the time course of choroidal thickness changes in response to defocus, have illustrated that these changes occur within minutes of exposure. When the defocus is imposed for a day, it significantly disrupts the normal diurnal rhythms in choroidal thickness and axial length with predictable patterns of change depending on the sign of the defocus. Lens designs in accordance with the present invention were evaluated in a similar fashion and found to positively influence choroidal thickness changes as shown in FIG. 6 which shows the change in axial length relative to power in diopters. As one can see the change in axial length is inversely proportional to increasing positive power from −3.0 through plano ("pl") up to +10.0 diopters.

Figure 7A:
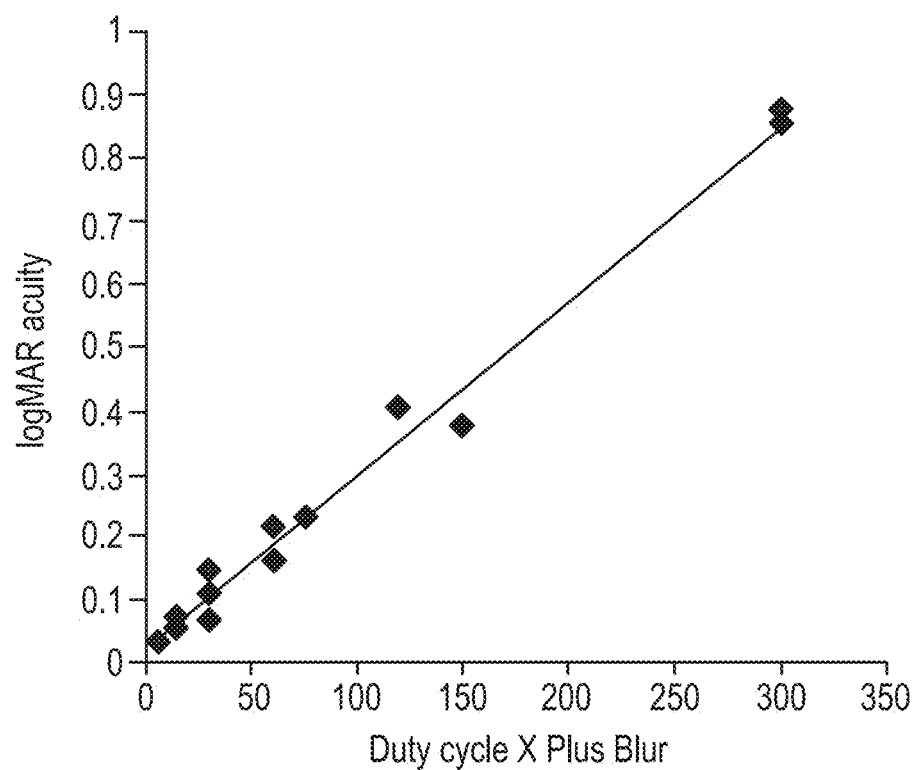
FIG. 7a shows a graph of the product of Duty cycle multiplied by plus power (ie: induced blur) in units of Percent*Diopter compared to the loss of visual acuity.
Figure 7B:
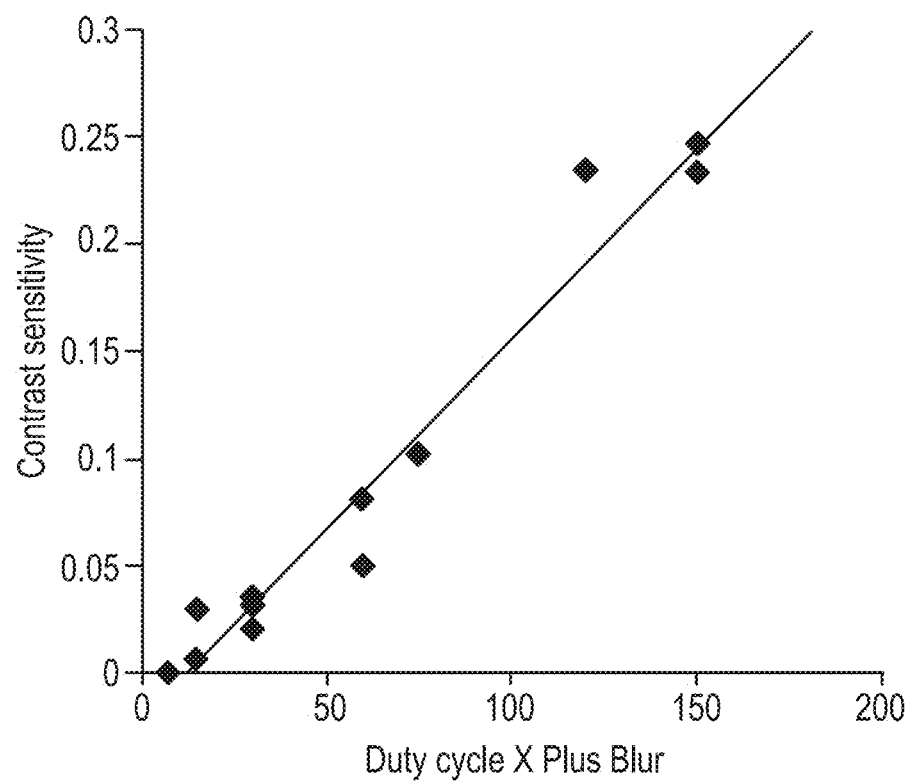
FIG. 7b shows a graph of the product of Duty cycle multiplied by plus power (ie: induced blur) in units of Percent*Diopter compared to contrast sensitivity.

Given that both duration (ie: duty cycle) of plus power and the level of plus power are directly proportional to therapeutic effectiveness of treating myopia progression we can recreate graphs shown in FIGS. 3A and 3B. We accomplish this by comparing the visual acuity (See FIG. 7A) and contrast sensitivity (See FIG. 7B) to the product of Duty Cycle multiplied by the level of plus power (ie: blur). As one can see in both FIGS. 7A and 7B there is an excellent linear fit of the data between the product of the two to both loss of visual acuity and contrast sensitivity. While the increasing value of the product of Duty cycle multiplied by Plus power results in increased therapeutic effect, we have to take into effect the increasing loss of visual acuity as well. As such it is important to limit the loss of visual acuity to three lines or less (0.3 log MAR acuity) and preferably two lines or less (ie: 0.2 log MAR acuity). As shown in FIG. 7A, using a loss of three lines or less one can then determine the upper limit for the product of Duty cycle multiplied by Plus power. In this case a upper limit of a loss of 3 lines roughly equates to a value of 100 Percent*Diopters (Duty cycle multiplied by Plus power). Since visual performance can be impacted by both visual acuity and contrast sensitivity, returning to FIG. 7B, and using this value of 100 Percent*Diopters (Duty cycle multiplied by Plus power) one can also determine the corresponding Contrast sensitivity value. In this case using the Duty cycle multiplied by Plus power value of 100 Percent*Diopters, equates to a Contrast Sensitivity value of approximately 0.15 which is acceptable amongst a significant portion of eye care professionals. Given that lenses with plus power as low as 0.5 Diopters, and duty cycles as low as 10% show a therapeutic effective, we can also define a preferred lower limit of Duty cycle multiplied by Plus power of approximately 5 Percent*Diopters. Table 3 below shows some exemplary combinations of the preferred plus power and duty cycle that satisfies the conditions for both upper and lower limits of Duty cycle multiplied by Plus power, with the understanding that combinations of values that fall between these upper and lower limits would also satisfy the conditions of therapeutic effectiveness with acceptable visual performance in accordance with the present invention.

TABLE 3

| Limit (Product of Duty Cycle × Plus Power) | Duty Cycle | Plus Power | Resulting loss of VA | Resulting loss of Contrast Sensitivity | Modulation Frequency |
|---|---|---|---|---|---|
| Lower (5) | 10% | 0.5 | <1 line | ~0 | >Flicker fusion rate |
| Lower (5) | 5% | 1.0 | <1 line | ~0 | >Flicker fusion rate |
| Lower (5) | 2.5% | 2.0 | <1 line | ~0 | >Flicker fusion rate |
| Upper (100) | 10% | 10.0 | 3 lines or less | 0.15 | >Flicker fusion rate |
| Upper (100) | 20% | 5.0 | 3 lines or less | 0.15 | >Flicker fusion rate |
| Upper (100) | 30% | 3.3 | 3 lines or less | 0.15 | >Flicker fusion rate |

Although shown and described in what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An ophthalmic lens system including circuitry for electronically oscillating focus of incoming light upon retina wherein the focus is modulated at a level that is imperceptible to a wearer of the lens while providing acceptable vision at near and far viewing distances, the ophthalmic lens system comprising: a first lens; a variable focus optic within the first lens, wherein the variable focus optic is configured to be tuned to achieve at least one focus state wherein incoming light is focused on a retina of a wearer to correct myopia or hyperopia of said wearer, and at least one defocus state wherein incoming light is focused in front of the retina to create myopic blur for said wearer to at least one of slowing, retarding, reversing or preventing myopia development or progression by temporally modulating a transmitted retinal image, or a portion thereof, in terms of power/focus in order to achieve a fleeting temporal defocus imperceptible to the brain while causing a change in eye growth due to the introduction of positive defocus in the retinal image while simultaneously providing acceptable vision at near and far viewing distances; a controller configured to control the variable focus optic and having a selectable duty cycle, the controller adapted to cause enabling the variable focus optic to alternate between the at least one focus state and the at least one defocus state at a rate sufficiently high to be imperceptible to the user, generate a series of wavefront patterns of both plus power and plano power alternatively displayed by the transmissive high speed tunable optics; and a power supply for energizing the variable focus optic and the controller.

2. The ophthalmic lens system according to claim 1, wherein the at least one focus state achieves extended depth of focus.

3. The ophthalmic lens system according to claim 1, further comprising first and second focal states, said first focus state correcting myopia and said second focus state correcting hyperopia wherein the focus is modulated to allow simultaneously good near and distance vision in presbyopic wearers.

4. The ophthalmic lens system according to claim 1 wherein the change in focus may vary from 0.50 Diopter to 20 Diopters.

5. The ophthalmic lens system according to claim 1, wherein the rate of oscillation of focus is above the human critical flicker fusion frequency.

6. The ophthalmic lens system according to claim 1, wherein the proportion of time for which the defocus state is presented to the wearer is from 1 percent to 75 percent.

7. The ophthalmic lens system according to claim 1, wherein the variable focus optic comprises a liquid crystal insert.

8. The ophthalmic lens system according to claim 1, wherein the variable focus optic comprises a liquid meniscus insert.

9. The ophthalmic lens system according to claim 1, wherein 90 percent of the change in focus within the first lens occurs in less than 20 ms.

10. The ophthalmic lens system according to claim 1, wherein the degree of change in focus may vary across the first lens.

11. The ophthalmic lens system according to claim 1, wherein the first lens is an electronic contact lens.

12. The ophthalmic lens system according to claim 1, wherein the first lens is an electronic spectacle lens.

13. The ophthalmic lens system according to claim 1, wherein the first lens is an electronic intraocular lens.

14. The ophthalmic lens system according to claim 1, further comprising a second lens having an independent variable focus optic configured to operate at least one of independently, synchronously, or synergistically relative to the first lens.

15. The ophthalmic lens system according to claim 1, wherein 90 percent of the change in focus within the first lens occurs in less than 10 ms.

16. An ophthalmic lens system for treating myopia progression in a patient comprising a first lens to be worn in front of, on or implanted in an eye; a variable focus optic within the lens, wherein the variable focus optic is configured to be tuned to achieve at least one focus state wherein incoming light is focused on a retina of a wearer to correct myopia or hyperopia of said user, and at least one defocus state wherein incoming light is focused in front of the retina to create myopic blur for said wearer to at least one of slowing, retarding, reversing or preventing myopia development or progression by temporally modulating a transmitted retinal image, or a portion thereof, in terms of power/focus in order to achieve a fleeting temporal defocus imperceptible to the brain while causing a change in eye growth due to the introduction of positive defocus in the retinal image while simultaneously providing acceptable vision at near and far viewing distances; a controller in electrical communication with the variable focus optic configured adapted to cause enabling the variable focus optic to alternate between the at least one focus state and the at least one defocus state at a rate sufficiently high to be imperceptible to the user, wherein the controller has to control the variable focus optic and having a selectable duty cycle wherein said duty cycle includes imperceptible pulses of defocus having a duty cycle ranging from 5 to 90 percent, the controller enabling the variable focus optic to generate a series of wavefront patterns of both plus power and plano power alternatively displayed by the transmissive high speed tunable optics; and a power supply for energizing the variable focus optic and the controller.

17. The ophthalmic lens system according to claim 16 wherein the duty cycle ranges from 10 to 30 percent.

18. The ophthalmic lens system according to claim 16 wherein a change in visual acuity is approximately 0.4 or less in logMAR units.

19. The ophthalmic lens system according to claim 16 wherein a change in Weber contrast sensitivity is 0.15 or less.

20. The ophthalmic lens system according to claim 16 wherein a change in visual acuity is approximately 0.4 or less in logMAR units as compared to baseline and a change in Weber contrast sensitivity is 0.15 or less.

21. The ophthalmic lens system according to claim 16 wherein the value of the percent duty cycle multiplied by a defocus plus power ranges from 5 to 100 Percent*Diopter.

* * * * *